United States Patent [19]

De Vincentiis

[11] 4,386,070
[45] May 31, 1983

[54] PHARMACEUTICAL COMPOSITIONS ENDOWED WITH AN ANTIBACTERIAL ACTIVITY AND THEIR USE IN THE TREATMENT OF INFECTIONS DUE TO GRAM-POSITIVE AND GRAM-NEGATIVE PATHOGENS

[75] Inventor: Leonardo De Vincentiis, Rome, Italy

[73] Assignee: Ausonia Farmaceutici S.R.L., Pomezia-Rome, Italy

[21] Appl. No.: 238,811

[22] Filed: Feb. 27, 1981

Related U.S. Application Data

[63] Continuation-in-part of Ser. No. 84,539, Oct. 15, 1979, abandoned.

[30] Foreign Application Priority Data

Oct. 20, 1978 [IT]   Italy ............................... 28934 A/78
Sep. 25, 1979 [IT]   Italy ............................... 25973 A/79

[51] Int. Cl.$^3$ ...................... A61K 35/00; A61K 31/54; A61K 31/435; A61K 31/70

[52] U.S. Cl. ................................. 424/114; 424/246; 424/256; 424/180; 424/227; 424/251; 424/258

[58] Field of Search ...................... 424/114, 246, 256

[56] References Cited

PUBLICATIONS

Chemical Abstracts 75:101306h (1971).
Chemical Abstracts 87:111194g (1977).
Chemical Abstracts 87:177610w (1977).

*Primary Examiner*—Jerome D. Goldberg
*Attorney, Agent, or Firm*—Bucknam and Archer

[57] ABSTRACT

Pharmaceutical compositions consisting of an antibiotic (cephalosporins, tetracyclines, kanamycin) associated with a heterocyclicic β-ketoacid (nalidixic acid, oxolinic acid, cinoxacine, piromidic acid, pipemidic acid) are endowed with a marked synergism against Gram-positive and Gram-negative pathogens as well with a particularly relevant efficacy against antibiotic-resistant strains.

2 Claims, No Drawings

PHARMACEUTICAL COMPOSITIONS ENDOWED WITH AN ANTIBACTERIAL ACTIVITY AND THEIR USE IN THE TREATMENT OF INFECTIONS DUE TO GRAM-POSITIVE AND GRAM-NEGATIVE PATHOGENS

This is a continuation-in-part of our earlier U.S. Ser. No. 084,539 filed Oct. 15, 1979, which is incorporated herein by reference now abandoned.

The present invention concerns pharmaceutical compositions endowed with an antibacterial activity against both Gram-positive and Gram-negative organisms, consisting of an antibiotic associated with a heterocyclic β-keto-acid characterized by the following formula (I):

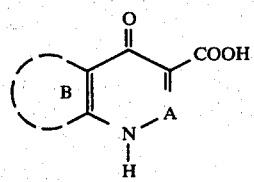

where A represents either a CH group or a nitrogen atom; B represents a benzene, azine or diazine group carrying possibly substituent groups such as $C_1$–$C_4$ alkyl groups, $C_1$–$C_4$ alkoxyl groups, halogen atoms, dioxymethylene groups or saturated heterocyclic rings; R is either a hydrogen atom or a $C_1$–$C_4$ alkyl group.

According to a preferred aspect of the invention, B takes such structural aspects as to provide, together with the related condensated ring, quinoline, cinnoline, naphthiridine, pyrido 2,3-d pyrimidine skeletons while R takes the significance of an ethyl group.

Specifically, the compounds characterized by the formula (I), as used in the compositions of the present invention, are represented by nalidixic acid (Ia), oxolinic acid (Ib), cinoxacine (Ic), piromidic acid (Id), pipemidic acid (Ie):

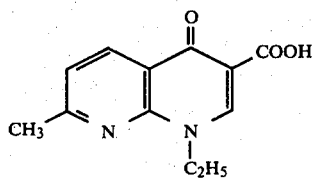

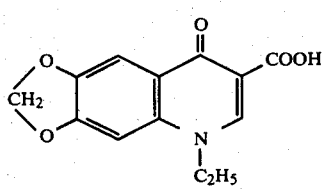

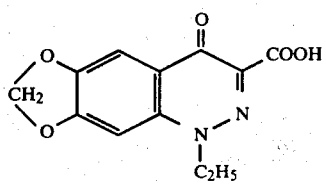

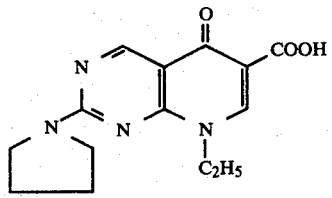

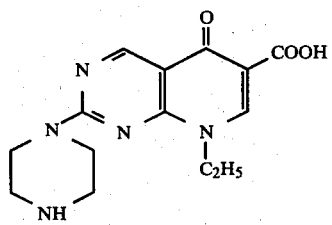

According to a more preferred aspect, the invention concerns pharmaceutical compositions consisting of a cephalosporin associated with nalidixic or oxolinic acid. More particularly, the invention concerns pharmaceutical compositions consisting of pivcephalexin and nalidixic acid, or of pivcephalexin and oxolinic acid.

On a general line, the antibiotic used as a component of the present compositions can be represented by any antibiotic; according to a preferred aspect of the invention, antibiotics of the family of tetracyclines, kanamycin, oleandomycin, and particularly cephalosporins can be used for the purpose.

The compositions of the present invention were found to be endowed with a marked synergism against Gram-positive and Gram-negative pathogens as well as with a particularly relevant efficacy against antibiotic-resistant strains.

It is known that the pathogens' resistance to antibiotics has been taking an ever increasing relevance, and that an ever increasing effort was dedicated in these recent years to the discovery of antibacterial agents particularly effective from this standpoint.

Therefore, according to the invention, the synergic compositions constitute an actual first rate therapeutic progress since, as already mentioned, but only enable to obtain a bacterial inhibition markedly higher than that expected on the basis of a simple effect of additivity of the two components, but enable essentially to inhibit antibiotic-resistant strains.

Therefore, the invention also concerns the use of the above mentioned compositions for the treatment of all infections due to Gram-positive and Gram-negative pathogens.

In the scope of the invention, the term "use" intends all the operations pertaining to the preparation of the components of the combination, to their purification, to their formulation as pharmaceutical dosage forms suited for administration, and/or to their packaging into containers suited for their administration.

According to the invention, the particular efficiency of the mentioned compositions against antibiotic-resistant strains is likely to be ascribed to an inhibited transfer of resistance genetic factors by the β-ketoacids characterized by the general formula (I); however, the present invention is not to be considered as associated with the above mentioned interpretation or with other possible interpretations of the experimental data.

The properties of the compositions according to the invention are illustrated by the below reported examples, that are no way limitative of the scope of the invention. The stability of said compositions was initially investigated, as appears evident from the below reported examples 1 and 2.

EXAMPLE 1

Stability of Pivcephalexin and Nalidixic Acid Mixtures (A) An ethanol solution of pivcephalexin hydrochloride (cephalexin pivaloyloxymethyl ester) is prepared, characterized by a concentration of 10 mcg/ml. In agreement with the data available in current literature, the UV spectrum of the solution shows a maximum absorption at 254 nm and a minimum centered at 240 nm.

(B) Moreover, an ethanol solution of nalidixic acid is prepared,

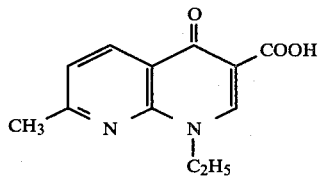

characterized by a concentration of 5 mcg/ml. The UV spectrum of the solution shows two characteristic absorption maxima centered at 330 nm and 257 nm respectively.

(C) An ethanol solution is prepared containing pivcephalexin 10 mcg/ml and nalidixic acid 5 mcg/ml. Thereafter a UV differential scanning is carried out between the solution (A) and the solution (C) as well as between the solution (B) and the solution (C) respectively. No change is observed in the spectrum, either just after the preparation of the solution (C) or at subsequent one-hour intervals for four consecutive hours: this evidence demonstrates both the absence of interactions and the perfect stability of the mixture.

Identical results are obtained when the ratios between pivcephalexin and nalidixic acid are varied from 2:1 to 1:1 and 5:1 respectively.

EXAMPLE 2

Stability of Pivcephalexin and Oxolinic Acid Mixtures

The procedure is as same as that shown in the Example 1, replacing however nalidixic acid with oxolinic acid.

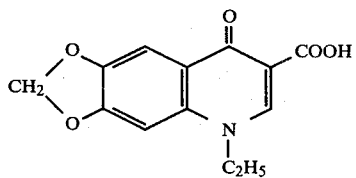

Also in this case the perfect stability of the mixture is demonstrated by the results of the spectral differential scanning between a solution containing pivcephalexin 10 mcg/ml or oxolinic acid 5 mcg/ml and a solution containing pivcephalexin 10 mcg/ml+oxolinic acid 5 mcg/ml.

Same results are also provided by the examination of analogous mixtures, for example mixtures of pivcephalexin with pipemidic acid and piromidic acid as well as of mixtures of cephadroxyl and cephalexin with either pipemidic, piromidic, oxolinic and nalidixic acids or with cinoxacine.

The better antibacterial properties of the composition, according to the invention, are pointed out by the values of the minimum inhibiting concentrations of various antibiotics, of the compounds characterized by the general formula (I) as well as of the combinations antibiotic+compound characterized by the formula (I) in a 1:1 ratio.

MATERIALS AND METHODS

The M.I.C. (Minimum Inhibiting Concentration), ie the lowest concentration of compound able to inhibit the bacterial growth, was established on 62 strains of pathogens (both Gram-positive and Gram-negative) subdivided as follows: 16 strains of Staphylococcus aureus, 1 strain of B. subtilis, 1 strain of B. megatherium, 1 strain of B. cereus ATCC 9341, 4 strains of Streptococcus faecalis, 1 strain of Serratia marcescens, 9 strains of Escherichia coli, 5 strains of Klebsiella pneumoniae, 6 strains of Salmonella spp., 2 strains of Shigella spp., 9 strains of Proteus spp., and 3 strains of Pseudomonas aeruginosa.

All the strains were seeded in Tripticase Soy Broth B.B.L. (Baltimora Biological Laboratory): a broth culture of each of them was obtained after an 18-hour incubation in a thermostat at 34° C.

Moreover the antibiotic, the compound (I), and their related mixture formulated in a 1:1 ratio, were dissolved in a pre-established quantity in the same culture medium: the related stock solutions were obtained.

From said stock solutions, various serial two-fold dilutions were made in various series of test-tubes, each test-tube containing 5 ml of fluid for each concentration of each single antibiotic, for their mixture and for all the investigational bacterial strains respectively. Said strains were seeded with 0.05 ml of broth culture in each test-tube.

The related results were read after thermostatization of all the system at 37° C. for 18 hours; the M.I.C., ie the Minimum Inhibiting Concentration of the antibiotic, of the compound(I), and of their related concentration, able to inhibit the growth of the seeded pathogen, was established for each bacterial strain.

The results obtained by the determination of the Minimal Inhibiting Concentration (M.I.C.) are shown in the attached Tables.

Table 1 shows the example of the oxolinic acid-cephalexin combination that, although used at the start in the form of pivaloyloxymethylester, is actually present in the cultures in the form of cephalexin and is assessed as such in expressing the concentrations.

TABLE 1

| M.I.C. as mcg/ml | Oxolinic Acid (ox) % | Cephalexin (C) % | Ox + C (1:1) % |
|---|---|---|---|
| 0.78 | 25 | | 15 |
| 1.56 | 40 | 25 | 35 |
| 3.12 | 45 | 45 | 75 |
| 6.25 | 55 | 65 | 80 |
| 12.50 | 70 | 75 | 80 |
| 25 | 70 | 85 | 90 |
| 50 | 95 | 85 | 100 |
| 100 | 95 | 100 | 100 |
| 200 | 100 | 100 | 100 |
| 400 | 100 | 100 | 100 |
| 800 | 100 | 100 | 100 |

Table 1 shows, for example, that the percentage of strains inhibited at the concentration of 3.12 mcg/ml, ie the concentration usually detectable in the biological fluids after the administration of antibacterial agents, is markedly higher in the case of the combination (75 percent) than in the case of the single components (45 percent). In other words, 1.56 mcg/ml of cephalexin+1.56 mcg/ml of oxolinic acid produce an effect markedly more favorable than that resulting from 3.12 mcg/ml of cephalexin or oxolinic acid. Analogous results are obtained at higher concentrations, although obviously the synergic effect is not any more detectable starting from concentrations at which the single components already begin producing an inhibitory effect in 100 percent of the strains.

Table 2 concerns the example of the combination between cephalexin (used as pivcephalexin, see above) and nalidixic acid.

TABLE 2

| M.I.C. as mcg/ml | Nalidixic Acid (NAL) % | Cephalexin (C) % | NAL + C (1:1) % |
|---|---|---|---|
| 0.78 | 30.9 | | |
| 1.56 | 64.2 | 2.38 | 19.04 |
| 3.12 | 76.1 | 38.09 | 52.3 |
| 6.25 | 80.9 | 64.2 | 85.7 |
| 12.50 | 83.3 | 76.1 | 88 |
| 25 | 85.7 | 83.3 | 90.4 |
| 50 | 90.4 | 83.3 | 92.8 |
| 100 | 90.4 | 85.7 | 100 |
| 200 | 92.8 | 90.4 | 100 |
| 400 | 95.2 | 92.8 | 100 |
| 800 | 97.6 | 92.8 | 100 |

Apparently, the results shown in Table 2 prove lower than those shown in Table 1. It shall be however underlined in this connection that, even starting from the concentration of 100 mcg/ml, the combination inhibits 100 percent of the strains examined while the single components, even at concentration eight times higher, still allow the survival of the most harmful strains, ie those very strains that, because of their resistance, cause latent and chronic infection characterized by recurrent flare-ups. One of the most relevant advantages of the combinations, according to the invention, just consists in eradicating said type of strains.

The experimentally obtained M.I.C. value for the investigational combination shall be compared with the M.I.C. values calculated on the basis of a strictly additive action of the two combined antibiotics (expected M.I.C.) in order to assess the synergism between the components of the combination.

The following basic expression, developed by CIMMINO et al. (Antibiot.Ann., 1957/58, pages 708–715) was used to establish the expected M.I.C. values:

$$C = \frac{2\,Cr \times Co}{Cr + Co}$$

where
Cr=M.I.C. of the compound characterized by the formula (I);
Co=M.I.C. of the antibiotic
C=Expected M.I.C. of the combination in a 1:1 ratio correspondent to a strictly additive action of the two antibiotics.

Now, the ratio between the expected M.I.C. value and the determined M.I.C. value enables to assess the combined effect of the two antibiotics, considering it as synergic when said ratio is higher than the unit.

Tables 3, 4, 5 and 6 show the results obtained. Tables 3 and 4 consider the effects produced on the Gram-positive pathogens by the combinations cephalexin-oxolinic acid and cephalexin-nalidixic acid respectively; tables 5 and 6 consider the effects produced by said mentioned combinations on Gram-negative pathogens.

TABLE 3

| | GRAM-POSITIVE PATHOGENS | (OX) OXOLINIC ACID | (C) CEPHALEXIN | OX + K (1:1) | | |
|---|---|---|---|---|---|---|
| | | | | Expected | determined | Expected/determined |
| 1 | Staphylococcus aureus 1 | 12.5 | 3.12 | 4.99 | 1.56 | 3.20 |
| 2 | Staphylococcus aureus 2 | 0.78 | 6.25 | 1.39 | 3.12 | 0.40 |
| 3 | Staphylococcus aureus 3 | 12.5 | 6.25 | 8.33 | 3.12 | 2.77 |
| 4 | Staphylococcus aureus 4 | 0.78 | 1.56 | 1.04 | 1.56 | 0.76 |
| 5 | Staphylococcus aureus 5 | 0.78 | 3.12 | 1.24 | 1.56 | 0.80 |
| 6 | Staphylococcus aureus 6 | 6.25 | 1.56 | 2.50 | 3.12 | 0.80 |
| 7 | Staphylococcus aureus 7 | 50 | 1.56 | 3.03 | 3.12 | 1 |
| 8 | Staphylococcus aureus 8 | 6.25 | 1.56 | 2.50 | 3.12 | 0.80 |
| 9 | Staphylococcus aureus 9 | 12.5 | 1.56 | 2.77 | 1.56 | 1.8 |
| 10 | Staphylococcus aureus 10 | 50 | 6.25 | 11.1 | 3.12 | 3.6 |
| 11 | Staphylococcus aureus Rose | 0.78 | 3.12 | 1.24 | 0.70 | 0.8 |
| 12 | Staphylococcus aureus Smith | 1.56 | 3.12 | 2.08 | 3.12 | 1.8 |
| 13 | Streptococcus faecalis 1 | 50 | 100 | 66.7 | 25 | 2.7 |
| 14 | Streptococcus faecalis 2 | 200 | 100 | 133.3 | 50 | 2.7 |
| 15 | Streptococcus faecalis 3 | 50 | 25 | 33.3 | 25 | 1.3 |
| 16 | Streptococcus faecalis 4 | 50 | 100 | 66.7 | 25 | 2.7 |
| 17 | Bacillus cereus ATCC 9634 | 0.78 | 25 | 1.51 | 0.78 | 2 |
| 18 | Bacillus subtilis ATCC 6633 | 1.56 | 12.5 | 2.77 | 0.78 | 3.65 |
| 19 | Bacillus megatherium | 1.56 | 12.5 | 2.77 | 0.78 | 3.65 |
| 20 | Sarcina lutea ATCC 9341 | 3.12 | 6.25 | 4.16 | 1.56 | 2.7 |

TABLE 4

| | GRAM-POSITIVE PATHOGENS | (NAL) NALIDIXIC ACID | (C) CEPHALEXIN | NAL + C (1:1) | | |
|---|---|---|---|---|---|---|
| | | | | Expected | determined | Expected/determined |
| 1 | Staphylococcus aureus 1 | 200 | 3.12 | 6.14 | 1.56 | 4.94 |
| 2 | Staphylococcus aureus 2 | 25 | 6.25 | 10 | 3.12 | 3.2 |
| 3 | Staphylococcus aureus 3 | 200 | 6.25 | 12.1 | 3.12 | 3.8 |
| 4 | Staphylococcus aureus 4 | 200 | 1.56 | 3.10 | 3.12 | 1.99 |

TABLE 4-continued

| | GRAM-POSITIVE PATHOGENS | (NAL) NALIDIXIC ACID | (C) CEPHALEXIN | NAL + C (1:1) Expected | NAL + C (1:1) determined | Expected/determined |
|---|---|---|---|---|---|---|
| 5 | Staphylococcus aureus 5 | 25 | 3.12 | 5.55 | 3.12 | 1.88 |
| 6 | Staphylococcus aureus 6 | 200 | 1.56 | 3.10 | 1.56 | 2 |
| 7 | Staphylococcus aureus 7 | 400 | 1.56 | 3.11 | 1.56 | 2 |
| 8 | Staphylococcus aureus 8 | 200 | 1.56 | 3.10 | 3.12 | 1 |
| 9 | Staphylococcus aureus 9 | 200 | 1.56 | 3.10 | 3.12 | 1 |
| 10 | Staphylococcus aureus 10 | 400 | 6.25 | 12.3 | 1.56 | 7.9 |
| 11 | Staphylococcus aureus Rose | 25 | 3.12 | 5.55 | 1.56 | 3.56 |
| 12 | Staphylococcus aureus Smith | 25 | 3.12 | 5.55 | 6.25 | 0.9 |
| 13 | Streptococcus faecalis 1 | 800 | 100 | 177.8 | 100 | 1.8 |
| 14 | Streptococcus faecalis 2 | 800 | 100 | 177.8 | 200 | 0.9 |
| 15 | Streptococcus faecalis 3 | 800 | 25 | 48.5 | 50 | 1.9 |
| 16 | Streptococcus faecalis 4 | 800 | 100 | 177.8 | 50 | 3.6 |
| 17 | Bacillus cereus ATCC 9634 | 3.12 | 25 | 5.55 | 3.12 | 1.8 |
| 18 | Bacillus subtilis ATCC 6633 | 1.56 | 12.5 | 2.77 | 1.56 | 1.8 |
| 19 | Bacillus megatherium | 6.25 | 12.5 | 8.33 | 3.12 | 2.7 |
| 20 | Sarcina lutea ATCC 9341 | 3.12 | 6.25 | 4.16 | 3.12 | 1.3 |

TABLE 5

| | GRAM-NEGATIVE PATHOGENS | (OX) OXOLINIC ACID | (C) CEPHALEXIN | OX + C (1:1) Expected | OX + C (1:1) determined | Expected/determined |
|---|---|---|---|---|---|---|
| 3 | Escherichia coli 3 | 1.56 | 25 | 2.94 | 1.56 | 1.88 |
| 11 | Escherichia coli 11 | 3.12 | 12.5 | 4.99 | 3.12 | 1.60 |
| 19 | Klebsiella pneumoniae 3 | 3.12 | 12.5 | 4.99 | 0.78 | 6.40 |
| 30 | Proteus mirabilis 3 | 1.56 | 25 | 2.94 | 3.12 | 0.94 |
| 32 | Proteus rettgeri 1 | 200 | 400 | 266.7 | 100 | 2.67 |
| 33 | Proteus rettgeri 2 | 100 | 200 | 133.3 | 50 | 2.67 |
| 35 | Proteus vulgaris 2 | 3.12 | 12.50 | 4.99 | 6.25 | 0.80 |
| 36 | Proteus vulgaris 3 | 12.50 | 6.25 | 8.33 | 3.12 | 2.67 |
| 40 | Pseudomonas aeruginosa 1 | 800 | 800 | 1600 | 50 | 32 |
| 41 | Pseudomonas aeruginosa 2 | 800 | 800 | 1600 | 800 | 1 |
| 42 | Pseudomonas aeruginosa 3 | 800 | 800 | 1600 | 400 | 4 |

TABLE 6

| | GRAM-NEGATIVE PATHOGENS | (NAL) NALIDIXIC ACID | (C) CEPHALEXIN | NAL + C (1:1) Expected | NAL + C (1:1) determined | Expected/determined |
|---|---|---|---|---|---|---|
| 3 | Escherichia coli 3 | 1.56 | 25 | 2.94 | 1.56 | 1.88 |
| 16 | Enterobacter hafniae | 3.12 | 100 | 6.05 | 6.25 | 0.97 |
| 24 | Salmonella livingstone | 50 | 3.12 | 5.87 | 3.12 | 1.88 |
| 28 | Proteus mirabilis 1 | 6.25 | 12.5 | 8.33 | 6.25 | 1.33 |
| 29 | Proteus mirabilis 2 | 25 | 25 | 25 | 12.50 | 2 |
| 30 | Proteus mirabilis 3 | 6.25 | 25 | 10 | 6.25 | 1.60 |
| 32 | Proteus rattgeri 1 | 50 | 400 | 88.90 | 100 | 0.89 |
| 33 | Proteus rattgeri 2 | 12.50 | 200 | 23.53 | 3.12 | 7.54 |
| 35 | Proteus vulgaris 2 | 3.12 | 12.50 | 4.99 | 6.25 | 0.80 |
| 40 | Pseudomonas aeruginosa 1 | 800 | 800 | 1600 | 100 | 16 |
| 41 | Pseudomonas aeruginosa 2 | 400 | 800 | 640 | 200 | 3.20 |
| 42 | Pseudomonas aeruginosa 3 | 200 | 800 | 355.6 | 50 | 7.11 |

A critical survey of the results shown in all the attached four tables enables to realize that the combinations, according to the invention, prove highly effective essentially against the strains more resistant to the isolated components. These results are confirmed by the clinical experimentation, carried out on homogeneous groups of patients (males and females) affected by chronic urinary infections caused by cephalexin sensible and oxolinic acid sensible pathogens. A 2-weeks treatment with pivcephalexin (2 g/day of cephalexin) or with oxolinic acid (2 g/day) produced an urocultural negativeness on 36 subjects (A) in a group of 40 treated with pivcephalexin, and on 33 subjects (B) in a group of 40 treated with oxolinic acid. However, the bacteriological "follow up" effected two weeks after the end of the treatment revealed an infective relapse incidence of 10 subjects of the A-group, and of 14 subjects of the B-group. A third group of 40 patients was treated for 8 days with daily doses of 2 grams of an association consisting of cephalexin (as pivcephalexin) and oxolinic acid 1:1 (w/w). After the treatment, the bacteriological control was negative in 34 patients; however, the bacteriological "follow up" effected two weeks after the end of the treatment was positive only in 3 cases. Table 7 summarizes the results of this clinical experimentation and of a clinical test carried out in the same conditions, with the exception of the use of nalidixic acid instead of oxolinic acid.

TABLE 7

| Drug | No. of patients | Treatment length (days) | End of treatment No. of positive cases | End of treatment No. of negative cases | "Follow-up" No. of positive cases | "Follow-up" No. of negative cases |
|---|---|---|---|---|---|---|
| CE | 40 | 15 | 4 | 36 | 10 | 26 |

TABLE 7-continued

| Drug | No. of patients | Treatment length (days) | End of treatment No. of positive cases | End of treatment No. of negative cases | "Follow-up" No. of positive cases | "Follow-up" No. of negative cases |
|---|---|---|---|---|---|---|
| OX | 40 | 15 | 7 | 33 | 14 | 19 |
| CE + OX | 40 | 8 | 6 | 34 | 4 | 30 |
| NA | 40 | 15 | 6 | 34 | 13 | 21 |
| CE + NA | 40 | 8 | 7 | 33 | 4 | 29 |

CE = cephalexin, 2 g/day (as pivcephalexin)
OX = oxolinic aicd, 2 g/day
CE + OX = association 1:1, 2 g/day
NA = nalidixic acid, 2 g/day
CE + NA = association 1:1, 2 g/day
The drugs were administered orally, as tablets containing 500 mg of active principle.

The pharmaceutical compositions of the invention are formulated as tablets or capsules, containing 500–1000 mg of an association of antibiotic and β-ketoacid of the formula (I) in a ratio of 1:1 (w/w).

It shall be underlined that the results, shown in the case of the combinations (piv)cephalexin/oxolinic acid and (piv)cephalexin/nalidixic acid, are only reported as example. Other combinations proved similarly effective, as in the case of the combinations cephadroxyl/pipemidic acid; cephadroxyl/cinoxacine; cephadroxyl/nalidixic acid; pivcephalexin/pipemidic acid; cefatrizine/piromidic acid; cefatrizine/oxolinic acid; cefatrizine/pipemidic acid, and others.

I claim:

1. The method of treatment of bacterial infections of human beings, due to both Gram-positive and Gram-negative pathogens, which consists of orally administering to said human being a tablet or capsule containing 500–1000 mgs. of an association of a bacterial antibiotic which is cephalexin or pivcephalexin and a β-ketoacid which is nalidixic acid in the ratio of 1:1.

2. A pharmaceutical composition endowed with an antibacterial activity against Gram-positive and Gram-negative organisms, which comprises as active ingredients an antibiotic which is cephalexin or pivcephalexin and a β-ketoacid which is nalidixic acid in the ratio of 1:1 respectively by weight.

* * * * *